United States Patent [19]

Ohsumi et al.

[11] Patent Number: 5,189,040
[45] Date of Patent: Feb. 23, 1993

[54] PYRAZOLE DERIVATIVES, METHOD FOR PRODUCING THE SAME AND AGRICULTURAL AND/OR HORTICULTURAL FUNGICIDES CONTAINING THE SAME AS ACTIVE INGREDIENT

[75] Inventors: Tadashi Ohsumi, Darmstadt, Fed. Rep. of Germany; Makoto Fujimura, Tokyo; Miki Hayashi, Ikeda, both of Japan

[73] Assignee: Sumitomo Chemical Company, Limited, Osaka, Japan

[21] Appl. No.: 701,240

[22] Filed: May 16, 1991

[30] Foreign Application Priority Data

May 28, 1990 [JP] Japan .................................. 2-138717
Mar. 27, 1991 [JP] Japan .................................. 3-89952

[51] Int. Cl.$^5$ .................... A61K 31/505; C07D 403/12
[52] U.S. Cl. ........................ 514/269; 544/319; 544/320; 544/321; 544/333; 544/334; 544/335
[58] Field of Search .............. 544/319, 320, 321, 333, 544/334, 335; 514/269

[56] References Cited

FOREIGN PATENT DOCUMENTS 1125379 5/1989 Japan .

*Primary Examiner*—Mukund J. Shah
*Assistant Examiner*—Y. N. Gupta
*Attorney, Agent, or Firm*—Armstrong, Westerman, Hattori, McLeland & Naughton

[57] ABSTRACT

A compound having the formula [I]:

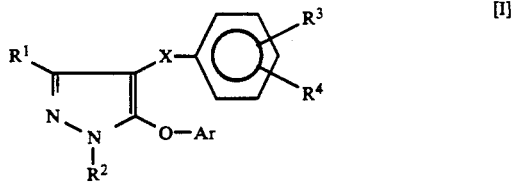

wherein $R^1$ is hydrogen atom or a lower alkyl group, $R^2$ is a lower alkyl group, $R^3$ and $R^4$ are the same or different each other and each is a hydrogen atom, a halogen atom, a lower alkyl group, a lower haloalkyl group or a lower alkoxy group, X is an oxygen atom, a sulfur atom or a methylene group, and Ar is a pyrimidine-4-yl group, a pyridine-2-yl group, a pyrazine-2-yl group or a pyridazine-3-yl group each of which may be substituted by one or two substituents selected from the group consisting of a halogen atom, a lower alkyl group, a lower alkoxy group and a nitro group, or a pyrimidine-2-yl group which is substituted by one or two substituents selected from the group consisting of a halogen atom, a lower alkyl group and a lower alkoxy group, a process for preparing the same and agricultural and/or horticultural fungicides containing the same as an active ingredient. According to the present invention, the excellent agricultural and/or horticultural fungicides can be provided.

12 Claims, No Drawings

PYRAZOLE DERIVATIVES, METHOD FOR PRODUCING THE SAME AND AGRICULTURAL AND/OR HORTICULTURAL FUNGICIDES CONTAINING THE SAME AS ACTIVE INGREDIENT

The present invention relates to pyrazole derivatives, a process for preparing the same and agricultural and/or horticultural fungicides containing the same as an active ingredient. More particularly, the present invention relates to a compound having the formula [I]:

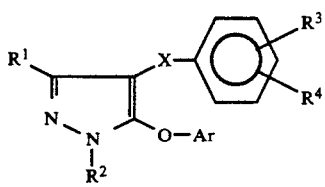

wherein $R^1$ is a hydrogen atom or a lower alkyl group, $R^2$ is a lower alkyl group, $R^3$ and $R^4$ are the same or different each other and each is a hydrogen atom, a halogen atom, a lower alkyl group, a lower haloalkyl group or a lower alkoxy group, X is an oxygen atom, a sulfur atom or a methylene group, and Ar is a pyrimidine-4-yl group, a pyridine-2-yl group, a pyrazine-2-yl group or a pyridazine-3-yl group each of which may be substituted by one or two substituents selected from the group consisting of a halogen atom, a lower alkyl group, a lower alkoxy group and a nitro group, or a pyrimidine-2-yl group which is substituted by one or two substituents selected from the group consisting of a halogen atom, a lower alkyl group and a lower alkoxy group; an agricultural and/or horticultural fungicidal composition which comprises as an active ingredient a fungicidally effective amount of said compound and an agriculturally and/or horticulturally acceptable carrier or diluent; a method for preventing plant diseases which comprises applying a fungicidally effective amount of said compound to plants; a use of said compound as an agricultural and/or horticultural fungicide and a process for preparing said compound, which comprises reacting a compound having the formula [II]:

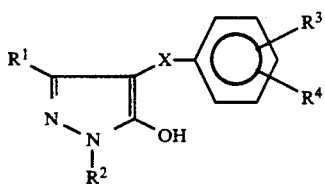

wherein $R^1$, $R^2$, $R^3$, $R^4$ and X are as defined in said compound, with a compound having the formula [III]:

Y—Ar [III]

wherein Y is a halogen atom and Ar is as defined in said compound.

Heretofore it has been known that a certain kind of pyrazole derivatives can be used as fungicides as described in Japanese Unexamined Patent Publication No. 125379/1989.

However, such compounds are not exactly sufficient as active ingredients in agricultural and/or horticultural fungicides.

It is an object of the invention is to provide pyrazole derivatives.

A further object of the invention is to provide agricultural and/or horticultural fungicides containing the same as an active ingredient.

It is still further object of the invention to provide a process for preparing the same.

It is another object of the invention to provide a method for preventing plant diseases by applying the same to plants.

It is another object of the invention to provide a use of the same as an agricultural and/or horticultural fungicide.

These and the other objects of the present invention will become apparent from the description hereinafter.

It has now been found that the pyrazole derivatives having the formula [I] have excellent fungicidal activity as shown below.

In accordance with the present invention, there are provided a compound having the formula [I]:

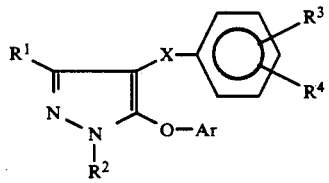

wherein $R^1$ is a hydrogen atom or a lower alkyl group, $R^2$ is a lower alkyl group, $R^3$ and $R^4$ are the same or different each other and each is a hydrogen atom, a halogen atom, a lower alkyl group, a lower haloalkyl group or a lower alkoxy group, X is an oxygen atom, a sulfur atom or a methylene group, and Ar is a pyrimidine-4-yl group, a pyridine-2-yl group, a pyrazine-2-yl group or a pyridazine-3-yl group each of which may be substituted by one or two substituents selected from the group consisting of a halogen atom, a lower alkyl group, a lower alkoxy group and a nitro group, or a pyrimidine-2-yl group which is substituted by one or two substituents selected from the group consisting of a halogen atom, a lower alkyl group and a lower alkoxy group being a pyrazole derivative (hereinafter also referred to as "the compound of the present invention"); an agricultural and/or horticultural fungicidal composition which comprises as an active ingredient a fungicidally effective amount of the same and an agriculturally and/or horticulturally acceptable carrier or diluent; a method for preventing plant diseases which comprises applying a fungicidally effective amount of the same to plants, a use of the same as an agricultural and/or horticultural fungicide and a process for preparing the same, which comprises reacting a compound having the formula [II]:

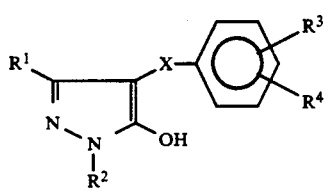

wherein R¹, R², R³, R⁴ and X are as defined above, with a compound having the formula [III]:

Y—Ar  [III]

wherein Y is a halogen atom and Ar is as defined above.

Hereinafter, the present invention is explained in detail. Namely the substituents R¹, R², R³, R⁴, X and Ar in the compound of the present invention are explained below.

It is perferable that the terms "a lower alkyl group" and "a lower alkoxy group" mean an alkyl group having 1 to 4 carbon atoms and an alkoxy group having 1 to 4 carbon atoms, respectively.

As a halogen atom a fluorine atom, a chlorine atom, a bromine atom and the like are exemplified.

As a lower haloalkyl group a trifluoromethyl group, a difluoromethyl group and the like are exemplified.

From the view point of fungicidal activity the followings can be found as to the compound of the present invention.

As the substituent R¹ a hydrogen atom or a methyl group is preferable, and a methyl group is more preferable. As the substituent R² a methyl group or an ethyl group is preferable. As the substituents R³ and R⁴ the combination of a 2-halogen atom and a hydrogen atom is preferable. As the substituent X a sulfur atom is preferable. As the substituent Ar a pyrimidine-4-yl group or a pyridine-2-yl group each of which may be substituted by one or two substituents selected from the group consisting of a halogen atom, a lower alkyl group, a lower alkoxy group and a nitro group, or a pyrimidine-2-yl group which is substituted by one or two substituents selected from the group consisting of a halogen atom, a lower alkyl group and a lower alkoxy group is preferable; a pyrimidine-4-yl group or a pyridine-2-yl group which may be substituted by one or two substituents selected from the group consisting of a halogen atom, or a lower alkyl group, a lower alkoxy group and a nitro group is more preferable; and a 2-halogenopyrimidine-4-yl group or a 6-halogenopyridine-2-yl group is especially preferable.

Typical examples of the compound of the present invention are shown in Table 1. The compound of the present invention is not limited to these compounds shown in Table 1.

TABLE 1

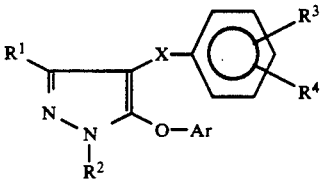

| R¹ | R² | R³ | R⁴ | Ar | X |
|---|---|---|---|---|---|
| CH₃ | CH₃ | 2-OCH₃ | H | 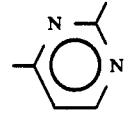 | S |
| CH₃ | CH₃ | H | 2-CH₃ | 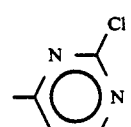 | S |
| CH₃ | CH₃ | 4-C₄H₉(n) | H | 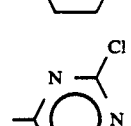 | S |
| CH₃ | CH₃ | 2-CH₃ | 4-CH₃ | 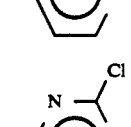 | S |
| CH₃ | CH₃ | 2-CH₃ | 6-CH₃ | 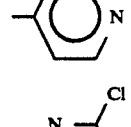 | S |
| CH₃ | CH₃ | 2-Cl | 6-Cl | 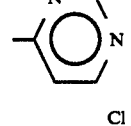 | S |

TABLE 1-continued
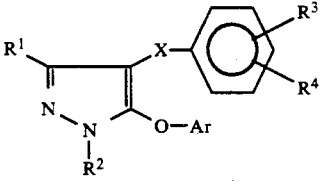
| R¹ | R² | R³ | R⁴ | Ar | X |
|---|---|---|---|---|---|
| CH₃ | CH₃ | 2-Cl | 5-Cl | 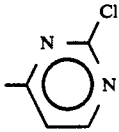 | S |
| CH₃ | CH₃ | 2-Cl | 4-Cl | 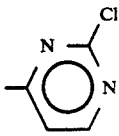 | S |
| CH₃ | CH₃ | H | 4-Cl | 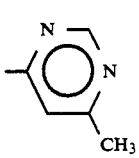 | S |
| CH₃ | CH₃ | H | 4-Cl | 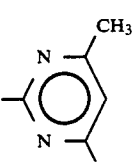 | S |
| H | CH₃ | H | 4-Cl | 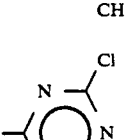 | S |
| CH₃ | CH₃ | 3-CH₃ | H | 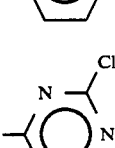 | O |
| CH₃ | CH₃ | H | 4-CH₃ | 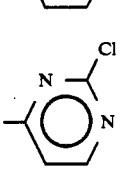 | O |
| H | CH₃ | 4-CH₃ | H | 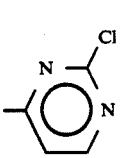 | O |
| CH₃ | CH₃ | 2-Cl | H | 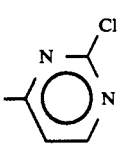 | S |

TABLE 1-continued

[Structure: pyrazole with R¹ at 3-position, R² on N, linked via X to phenyl ring bearing R³ and R⁴, and via O-Ar]

| R¹ | R² | R³ | R⁴ | Ar | X |
|---|---|---|---|---|---|
| CH₃ | CH₃ | H | 3-Cl | 2-chloro-4-methylpyrimidin-yl | S |
| CH₃ | CH₃ | 4-OCH₃ | H | 2-chloro-4-methylpyrimidin-yl | S |
| CH₃ | CH₃ | H | 4-OC₄H₉(n) | 2-chloro-4-methylpyrimidin-yl | S |
| CH₃ | CH₃ | H | 4-Cl | 4-OCH₃, 5-CH₃-pyrimidin-2-yl | S |
| CH₃ | CH₃ | 4-Cl | H | 4-OCH₃, 6-CH₃-pyrimidin-2-yl | S |
| CH₃ | CH₃ | H | 4-Cl | 4-OCH₃-pyrimidin-2-yl | S |
| CH₃ | CH₃ | H | H | 4-OCH₃-pyrimidin-2-yl | S |
| H | CH₃ | 4-Cl | H | 4-OCH₃-pyrimidin-2-yl | S |
| CH₃ | CH₃ | 4-Cl | H | 6-chloropyridazin-3-yl | S |

TABLE 1-continued

Structure: pyrazole with R¹ at 3-position, R² on N, X-linked aryl ring bearing R³ and R⁴, and O–Ar at 5-position.

| R¹ | R² | R³ | R⁴ | Ar | X |
|---|---|---|---|---|---|
| CH₃ | CH₃ | H | 4-Cl | 3-methyl-6-chloropyrazin-2-yl | S |
| CH₃ | CH₃ | H | H | 3-methyl-6-chloropyrazin-2-yl | S |
| H | CH₃ | H | H | 3-methyl-6-chloropyrazin-2-yl | S |
| CH₃ | CH₃ | 4-Cl | H | 2-chloro-6-methylpyrimidin-4-yl | S |
| CH₃ | CH₃ | H | 4-Cl | 2,6-dichloropyrimidin-4-yl (with methyl) | S |
| CH₃ | CH₃ | 4-Cl | H | 2-chloro-4-methyl-6-methylpyrimidinyl | S |
| CH₃ | CH₃ | H | H | 2-chloro-6-methylpyrimidin-4-yl | S |
| H | CH₃ | 4-Cl | H | 2-chloro-6-methylpyrimidin-4-yl | O |
| CH₃ | CH₃ | H | 4-Cl | 6-methyl-3-nitropyridin-2-yl | S |

TABLE 1-continued
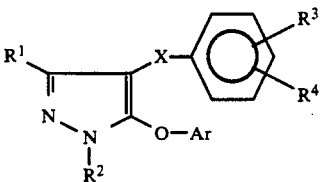
| R¹ | R² | R³ | R⁴ | Ar | X |
|---|---|---|---|---|---|
| CH₃ | CH₃ | 4-Cl | H | 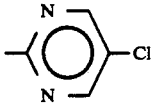 | S |
| CH₃ | CH₃ | H | 4-Cl | 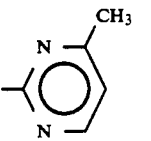 | S |
| CH₃ | CH₃ | 2-Cl | H | 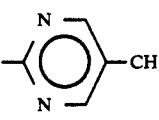 | S |
| CH₃ | CH₃ | 4-Cl | H | 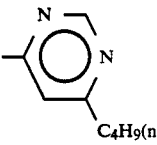 | S |
| CH₃ | CH₃ | H | 4-Cl | 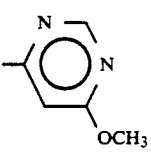 | S |
| CH₃ | CH₃ | 4-Cl | H | 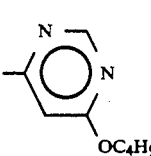 | S |
| CH₃ | CH₃ | H | 2-Cl | 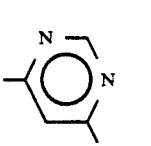 | O |
| CH₃ | CH₃ | 4-Cl | H | 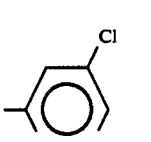 | S |
| CH₃ | CH₃ | H | 4-Cl | 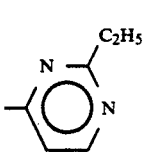 | S |

TABLE 1-continued

| R¹ | R² | R³ | R⁴ | Ar | X |
|---|---|---|---|---|---|
| CH₃ | CH₃ | H | 4-Cl | 4-methyl-2-(n-C₄H₉)-pyrimidinyl | S |
| H | CH₃ | 4-Cl | H | 4-methyl-2-(n-C₃H₇)-pyrimidinyl | S |
| H | CH₃ | H | H | 4-methyl-2-(O-n-C₃H₇)-pyrimidinyl | O |
| C₂H₅ | CH₃ | 2-Cl | H | 4-methyl-2-chloro-pyrimidinyl | S |
| C₂H₅ | CH₃ | 4-Cl | H | 4-methyl-2-chloro-pyrimidinyl | S |
| CH₃ | C₂H₅ | 2-Cl | H | 4-methyl-2-chloro-pyrimidinyl | S |
| CH₃ | C₃H₇(i) | 2-Cl | H | 4-methyl-2-chloro-pyrimidinyl | S |
| CH₃ | CH₃ | 2-Cl | H | 4-methyl-2-OCH₃-pyrimidinyl | S |
| CH₃ | CH₃ | 4-CF₃ | H | 4-methyl-2-chloro-pyrimidinyl | S |

TABLE 1-continued

Structure: pyrazole with R1 at 3-position, R2 on N1, X-aryl(R3,R4) at 4-position, O-Ar at 5-position

| R¹ | R² | R³ | R⁴ | Ar | X |
|---|---|---|---|---|---|
| CH₃ | C₂H₅ | 4-CF₃ | H | 4-methyl-2-chloropyrimidin-yl | S |
| CH₃ | CH₃ | 2-Cl | H | 4-methylpyrimidin-yl | S |
| CH₃ | CH₃ | 2-Cl | H | 4-methyl-2-chloropyrimidin-yl | CH₂ |
| CH₃ | CH₃ | 4-Cl | H | 4-methyl-2-chloropyrimidin-yl | CH₂ |
| CH₃ | CH₃ | 2-Cl | 4-Cl | 4-methyl-2-chloropyrimidin-yl | CH₂ |
| CH₃ | C₂H₅ | 2-Cl | H | 4-methyl-2-chloropyrimidin-yl | CH₂ |
| C₂H₅ | CH₃ | 2-Cl | H | 4-methyl-2-chloropyrimidin-yl | CH₂ |
| H | CH₃ | 2-Cl | 4-Cl | 4-methyl-2-chloropyrimidin-yl | CH₂ |
| H | C₂H₅ | 4-Cl | H | 4-methyl-2-chloropyrimidin-yl | CH₂ |

TABLE 1-continued
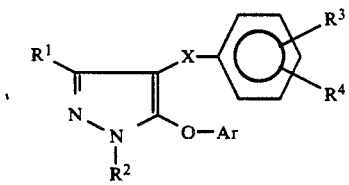
| R¹ | R² | R³ | R⁴ | Ar | X |
|---|---|---|---|---|---|
| CH₃ | CH₃ | 2-Cl | 4-Cl | 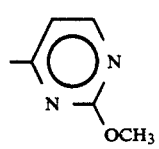 | CH₂ |
| CH₃ | CH₃ | 2-Cl | 4-Cl | 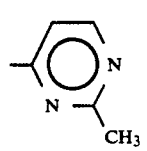 | CH₂ |
| CH₃ | C₂H₅ | 2-Cl | 4-Cl | 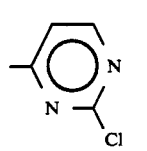 | CH₂ |
| CH₃ | CH₃ | 2-Cl | 4-Cl | 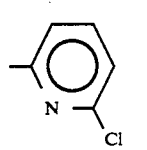 | CH₂ |
| CH₃ | CH₃ | 2-Cl | 4-Cl | 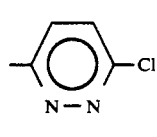 | CH₂ |
| CH₃ | CH₃ | 2-Cl | 4-Cl | 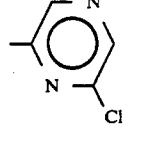 | CH₂ |
| CH₃ | CH₃ | 2-Cl | 4-Cl | 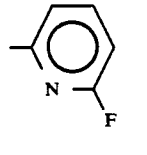 | CH₂ |
| CH₃ | C₂H₅ | 2-Cl | 4-Cl | 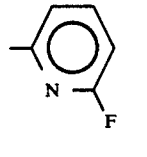 | CH₂ |
| CH₃ | CH₃ | 2-F | 4-Cl | 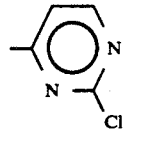 | CH₂ |

TABLE 1-continued
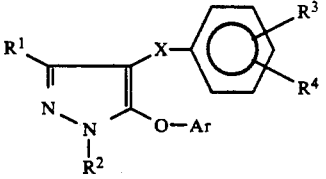
| R¹ | R² | R³ | R⁴ | Ar | X |
|---|---|---|---|---|---|
| CH₃ | CH₃ | 2-F | 4-F | 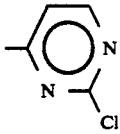 | CH₂ |
| CH₃ | CH₃ | 2-Br | H | 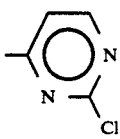 | CH₂ |
| CH₃ | CH₃ | 3-Cl | 4-Cl | 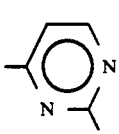 | CH₂ |
| CH₃ | CH₃ | 2-Cl | H | 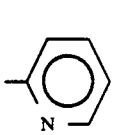 | S |
| CH₃ | C₂H₅ | 2-Cl | H | 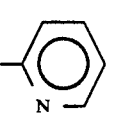 | S |
| CH₃ | CH₃ | 2-Cl | H | 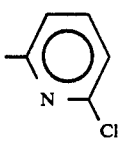 | S |
| CH₃ | CH₃ | 4-Cl | H | 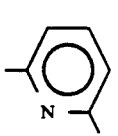 | S |
| CH₃ | CH₃ | 2-Cl | H | 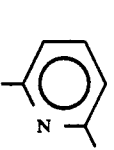 | S |
| CH₃ | CH₃ | 2-Cl | H | 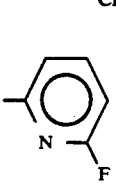 | S |

TABLE 1-continued

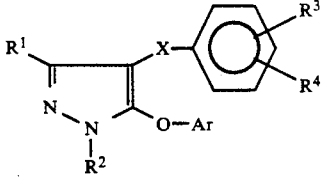

| R¹ | R² | R³ | R⁴ | Ar | X |
|---|---|---|---|---|---|
| CH₃ | C₂H₅ | 2-Cl | H | 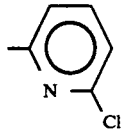 | S |
| CH₃ | C₃H₇(i) | 2-Cl | H | 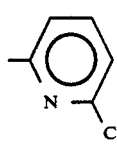 | S |
| C₂H₅ | CH₃ | 2-Cl | H | 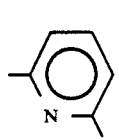 | S |
| H | CH₃ | 2-Cl | H | 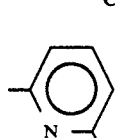 | S |

The compound of the present invention can control the following plant diseases;

Cereal diseases (*Pyricularia oryzae, Cochliobolus miyabeanus, Rhizoctonia solani, Erysiphe graminis* f. sp. *hordei, E. graminis* f. sp. *tritici, Pyrenophora graminea, P. teres, Gibberella zeae, Puccinia striiformis, P. graminis, P. recondita, P. hordei, Typhula* sp., *Micronectriella nivalis, Ustilago tritici, U. nuda, Pseudocercosporella herpotrichoides, Rhynchosporium secalis, Septoria tritici, Leptosphaeria nodorum*).

Fruit diseases (*Diaporthe citri, Elsinoe fawcetti, Penicillium digitatum, P. italicum, Sclerotinia mali, Valsa mali, Podosphaera leucotricha, Alternaria mali, A. kikuchiana, Venturia inaequalis, V. nashicola, Gymnosporangium haraeanum, Sclerotinia cinerea, Cladosporium carpophilum, Phomopsis* sp., *Elsinoe ampelina, Glomerella cingulata, Uncinula necator, Phakopsora ampelopsidis, Gloesporium kaki, Cercospora kaki, Mycosphaerella nawae*).

Vegetable diseases (*Colletotrichum lagenarium, Sphaerotheca fuliginea, Mycosphaerella melonis, Alternaria solani, A. japonica, Cladosporium fulvum, Phomopsis vexans, Erysiphe cichoracearum, E. pisi, Cercosporella brassicae, Puccinia allii, Cercospora kikuchii, Elsinoe glycines, Diaporthe phaseolorum, Colletotrichum lindemuthianum, C. tabacum, Mycosphaerella personatum, Cercospora arachidicola, Alternaria solani, Sphaerotheca humuli, Exobasidium reticulatum, Elsinoe leucospila, Alternaria longipes, Cercospora beticola*).

Ornamental diseases (*Diplocarpon rosae, Sphaerotheca pannosa, Septoria chrysanthemi-indici, Puccinia horiana*).

Diseases of various crops (*Botrytis cinerea, Sclerotinia sclerotiorum*), and so forth.

Then hereinafter the process for preparing the compound of the present invention is minutely explained. For instance, the compound of the present invention can be prepared by reacting a 5-hydroxypyrazole derivative having the formula [II]:

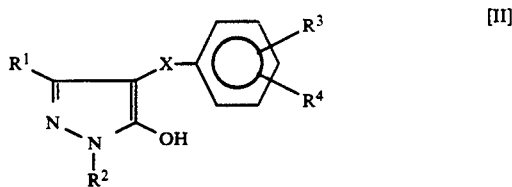

[II]

wherein R¹, R², R³, R⁴ and X are as defined above, with a halide having the formula [III]:

Y—Ar [III]

wherein Y is a halogen atom and Ar is as defined above.

In the reaction of the above-mentioned process a solvent is not always required. In case of using a solvent, as a used solvent there can be exemplified, for instance, hydrocarbons such as toluene, xylene and chlorobenzene, halogenated hydrocarbons such as dichloroethane, ethers such as diisopropyl ether and dioxane, esters such as ethyl acetate, nitriles such as acetonitrile, and polar solvents such as dimethyl sulfoxide and dimethylformamide, and the like.

Amount of the halide having the formula [III] used in the above reaction ranges from 1 to 20 equivalents per equivalent of the 5-hydroxypyrazole derivative having the formula [II]. Preferable range of the amount of the halide [III] is from 1 to 5 equivalents per equivalent of the 5-hydroxypyrazole derivative [II].

In the above reaction, reaction temperature is optional. Generally a temperature ranging from room temperature to 200° C. or a temperature at which a used solvent can be refluxed is preferred.

In the above reaction, it is preferable that the reaction time is from 30 minutes to 24 hours.

As occasion demands 1 to 5 equivalents of a base such as potassium carbonate, sodium hydroxide or sodium hydride can be employed per equivalent of the 5-hydroxypyrazole derivative [II].

After completing the reaction the desired compound can be obtained by carrying out usual work-up such as concentration of reaction solvent and extraction with an organic solvent. Further, as occasion demands, the desired compound can be purified by means of proceedings such as chromatography and recrystallization.

Corresponded to the substituent $R^1$ and/or the substituent X, the 5-hydroxypyrazole derivative having the formula [II] being a starting material of the compound of the present invention can be prepared, for instance, according to the following reaction scheme (i), (ii) or (iii).

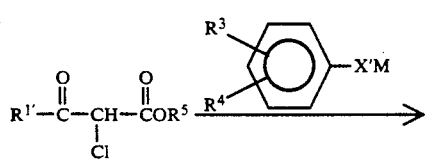

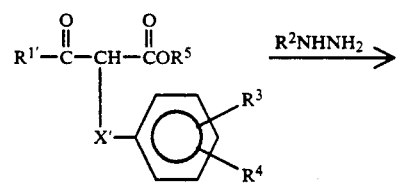

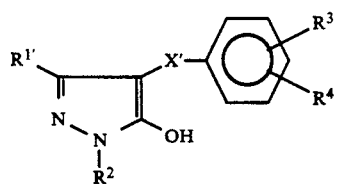

In the above reaction scheme (i), each of $R^{1'}$ and $R^5$ is a lower alkyl group, $X'$ is an oxygen atom or a sulfur atom, M is an alkaline metal, and $R^2$, $R^3$ and $R^4$ are as defined above.

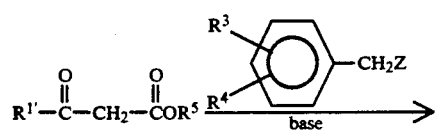

-continued

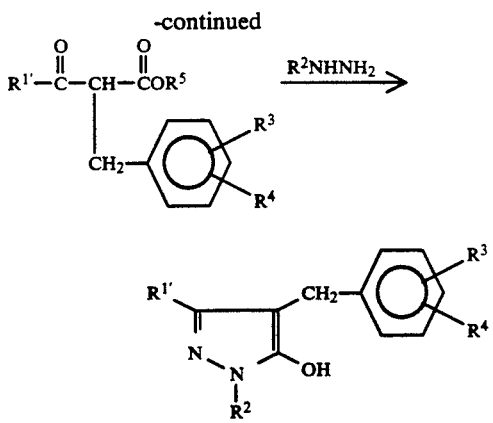

In the above reaction scheme (ii), Z is a halogen atom, and $R^{1'}$, $R^2$, $R^3$, $R^4$ and $R^5$ are as defined above.

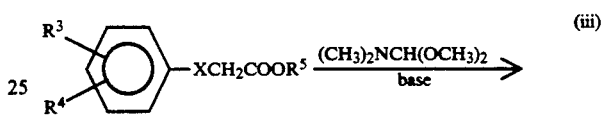

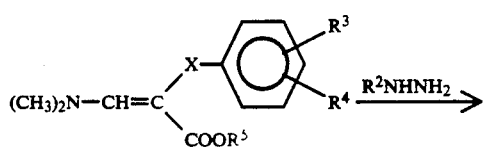

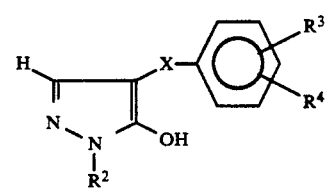

In the above reaction scheme (iii), $R^2$, $R^3$, $R^4$, $R^5$ and X are as defined above.

Also, in case that the halide having the formula [III] is commercially available, the compound on the market is used. Otherwise, conventionally the halide having the formula [III] can be easily prepared by halogenating a compound having hydroxy group being a precursor thereof.

In case of using the compound of the present invention as an active ingredient of fungicides, the compound of the present invention may be used without adding any other component. Generally the compound of the present invention is mixed with agriculturally and/or horticulturally acceptable carrier or diluent such as solid carrier or liquid carrier, surface active agent and/or other auxiliary substance for formulation to give emulsion, wettable powder, suspension, powder formulation, granule formulation, liquid formulation and the like. In this case the content of the compound of the present invention as the active ingredient in such formulation is within a range of 0.1 to 99.9% by weight, preferably 0.5 to 90% by weight.

Examples of the above-mentioned solid carrier are, for instance, fine powders or granules of kaolin clay, attapulgite clay, bentonite, acid clay, pyrophyllite, talc, diatomaceous earth, calcite, corncob powders, nutshell powders of walnut, urea, ammonium sulfate, synthetic hydrous silicate and the like.

As the liquid carrier, there may be exemplifed aromatic hydrocarbons (e.g. xylene, methylnaphthalene and the like), alcohols (e.g. isopropanol, ethylene glycol, 2-methoxyethanol and the like), ketones (e.g. acetone, cyclohexanone, isophorone and the like), vegetable oils (e.g. soybean oil, cotton seed oil and the like), dimethyl sulfoxide, acetonitrile, water, and the like.

Examples of the surface active agent used for emulsification, dispersion, spreading and the like are, for instance, anionic type agents (e.g. alkylsulfates, alkylarylsulfonates, dialkylsulfosuccinates, polyoxyethylenealkylaryl ether phosphates and naphthalenesulfonate formaldehyde condensations and the like), non-ionic agents (e.g. polyoxyethylene alkyl ethers, polyoxyethylene polyoxypropylene block copolymer, sorbitan fatty acid esters, polyoxyethylene sorbitan fatty acid esters and the like), and the like.

Examples of the auxiliary substance for formulation are, for instance, ligninsulfonates, alginates, polyvinyl alcohol, gum arabic, CMC (carboxymethyl cellulose), PAP (isopropyl acid phosphate) and the like.

In case that the compound of the present invention is employed as an agricultural and/or horticultural fungicide, examples of method for application are, for instance, foliar spraying, soil treatment, seed treatment and the like. However, the compound of the present invention shows sufficient fungicidal effect in any method for application which is usually utilized by a person skilled in the art.

The compound of the present invention can be employed as an agricultural and/or horticultural fungicide in plowed fields, paddy fields, orchards, tea plantations, pastures, lawns and the like, and also it can be expected that fungicidal potency of the compound of the present invention is reinforced by mixing with other agricultural and/or horticultural fungicide(s) and then employing the mixture. Further the compound of the present invention can be employed by mixing with insecticides, acaricides, nematocides, herbicides, plant growth regulators, fertilizers and/or the like.

In case of employing the compound of the present invention as an active ingredient in an agricultural and/or horticultural fungicide, the dosage rate of the active ingredient varies depending on subjected crops, objected plant diseases, occuring degree of plant diseases, formulation used, application method, application timing, weather conditions and the like. Generally, however, the dosage rate is from 0.1 to 100 grams, preferably from 0.2 to 20 grams of the active ingredient per are. In case that a formulation such as emulsion, wettable powder, suspension or liquid formulation which contains the compound of the present invention as an active ingredient is applied by diluting with water, application concentration of the compound of the present invention is from 0.001 to 1% by weight, preferable from 0.002 to 0.2% by weight. In case of applying a formulation such as powder formulation or granule formulation which contains the compound of the present invention as an active ingredient, the compound of the present invention is applied without dilution.

The present invention is more especially described and explained by means of the following Examples, Formulation Examples and Test Examples in which all parts are by weight unless otherwise noted. It is to be understood that the present invention is not limited to the Examples, the Formulation Examples and the Test Examples, and various changes and modifications may be made in the invention without departing from the spirit and scope thereof.

EXAMPLE 1

[Preparation of the compound No. 37]

A mixture of 1.1 g (4 mmol) of 1,3-dimethyl-4-(2-chlorophenylthio)-5-hydroxypyrazole and 5.0 g (34 mmol) of 2,6-dichloropyridine was refluxed with heating for 20 hours. After completing the reaction, the reaction mixture was purified by means of silica gel column chromatography (developing solution: ethyl acetate-hexane (2:1 v/v)) to give 0.40 g of 1,3-dimethyl-4-(2-chlorophenylthio)-5-(6-chloropyridine-2-yloxy)-pyrazole.

EXAMPLE 2

[Preparation of the compound No. 18]

A mixture of 2.4 g (10 mmol) of 1,3-dimethyl-4-(2-chlorophenylthio)-5-hydroxypyrazole, 1.5 g (10 mmol) of 2,4-dichloropyrimidine and 1.5 g (11 mmol) of potassium carbonate was refluxed for 1 hour in 10 ml of acetonitrile. After completing the reaction, the reaction mixture was poured into water, extracted with ethyl acetate and dried. Then the organic layer was concentrated. The residue was purified by means of silica gel column chromatography (developing solution: ethyl acetate-hexane (3:1 v/v)) to give 2.8 g of 1,3-dimethyl-4-(2-chlorophenylthio)-5-(2-chloropyrimidine-4-yloxy)-pyrazole.

EXAMPLE 3

[Preparation of the compound No. 13]

A mixture of 0.255 g (1.00 mmol) of 1,3-dimethyl-4-(4-chlorophenylthio)-5-hydroxypyrazole and 0.43 g (3.00 mmol) of 2-chloro-4,6-dimethylpyrimidine was heated on a bath of which temperature was 130° C. for 3 hours with stirring. After completing the reaction, the reaction mixture was purified by means of silica gel column chromatography (developing solution: ethyl acetate) to give 0.308 g of 1,3-dimethyl-4-(4-chlorophenylthio)-5-(4,6-dimethylpyrimidine-2-yloxy)-pyrazole.

EXAMPLE 4

[Preparation of the compound No. 15]

In 10 ml of acetonitrile were dissolved 0.220 g (1.00 mmol) of 1,3-dimethyl-4-(3-methylphenoxy)-5-hydroxypyrazole, 0.220 g (1.50 mmol) of 2,4-dichloropyrimidine and 0.210 g (1.50 mmol) of potassium carbonate. Thus obtained solution was stirred for 3 hours with refluxing. After completing the reaction, the reaction solution was poured into water, extracted with ethyl acetate and dried. The organic layer was concentrated. The residue was purified by means of silica gel column chromatography (developing solution: ethyl acetate-hexane (1:1 v/v)) to give 0.29 g of 1,3-dimethyl-4-(3-methylphenoxy)-5-(2-chloropyrimidine-4-yloxy)-pyrazole.

EXAMPLE 5

[Preparation of the compound No. 35]

A mixture of 0.5 g (2 mmol) of 1,3-dimethyl-4-(2-chlorophenylthio)-5-hydroxypyrazole and 0.97 g (10 mmol) of 2-fluoropyridine was refluxed with heating for 8 hours. After completing the reaction, the reaction mixture was purified by means of silica gel column chromatography (developing solution: ethyl acetate-hexane (3:2 v/v)) to give 0.17 g of 1,3-dimethyl-4-(2-chlorophenylthio)-5-(pyridine-2-yloxy)pyrazole.

EXAMPLE 6

[Preparation of the compound No. 28]

In 10 ml of acetonitrile were stirred 2.7 g (10 mmol) of 1,3-dimethyl-4-(2,4-dichlorobenzyl)-5-hydroxypyrazole, 1.5 g (10 mmol) of 2,4-dichloropyrimidine and 1.5 g (11 mmol) of potassium carbonate with refluxing for 3 hours. After completing the reaction, the reaction mixture was purified as the same manner as described in Example 4 to give 1.63 g of 1,3-dimethyl-4-(2,4-dichlorobenzyl)-5-(2-chloropyrimidine-4-yloxy)-pyrazole.

In Table 2 examples of the compound of the present invention are shown which were prepared according to the above-mentioned processes for preparation. Also, structure of the compound of the present invention was determined on the basis of spectral data of IR, NMR, MS and the like.

TABLE 2

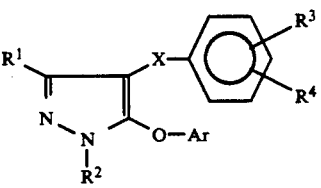

| Comp. No. | $R^1$ | $R^2$ | $R^3$ | $R^4$ | Ar | X | Property |
|---|---|---|---|---|---|---|---|
| 1 | $CH_3$ | $CH_3$ | 4-Cl | H | 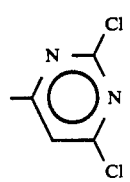 | S | mp 104.9° C. |
| 2 | $CH_3$ | $CH_3$ | H | 4-Cl | 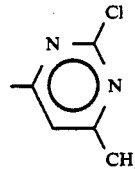 | S | mp 129.0° C. |
| 3 | $CH_3$ | $CH_3$ | 4-Cl | H | 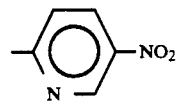 | S | mp 142.1° C. |
| 4 | $CH_3$ | $CH_3$ | H | 4-Cl | 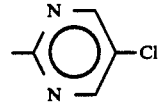 | S | mp 107.7° C. |
| 5 | $CH_3$ | $CH_3$ | 4-Cl | H | 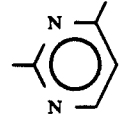 | S | mp 104.7° C. |
| 6 | $CH_3$ | $CH_3$ | H | 4-Cl | 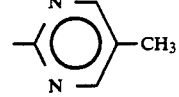 | S | mp 120.1° C. |
| 7 | $CH_3$ | $CH_3$ | 4-Cl | H |  | S | $n_D^{25.0}$ 1.5984 |

TABLE 2-continued
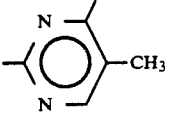
| Comp. No. | R¹ | R² | R³ | R⁴ | Ar | X | Property |
|---|---|---|---|---|---|---|---|
| 8 | CH₃ | CH₃ | H | 4-Cl | 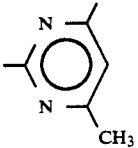 | S | mp 100.2° C. |
| 9 | CH₃ | CH₃ | 4-Cl | H | 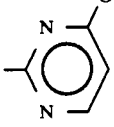 | S | $n_D^{25.0}$ 1.5936 |
| 10 | CH₃ | CH₃ | H | 4-Cl | 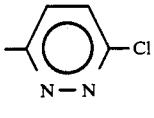 | S | $n_D^{19.5}$ 1.5987 |
| 11 | CH₃ | CH₃ | 4-Cl | H | 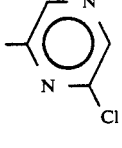 | S | mp 136.0° C. |
| 12 | CH₃ | CH₃ | H | 4-Cl | 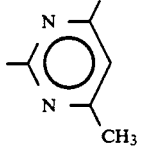 | S | mp 123.9° C. |
| 13 | CH₃ | CH₃ | H | 4-Cl | 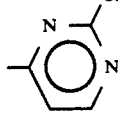 | S | mp 116.4° C. |
| 14 | H | CH₃ | H | 4-Cl | 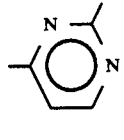 | S | $n_D^{19.0}$ 1.6173 |
| 15 | CH₃ | CH₃ | 3-CH₃ | H | 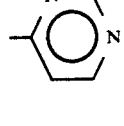 | O | $n_D^{20.5}$ 1.5695 |
| 16 | CH₃ | CH₃ | H | 4-CH₃ | 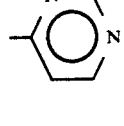 | O | mp 95.9° C. |

TABLE 2-continued

[Structure: pyrazole with R¹ at 3-position, N-N-R² at 1-position, X-phenyl(R³,R⁴) at 4-position, and O-Ar at 5-position]

| Comp. No. | R¹ | R² | R³ | R⁴ | Ar | X | Property |
|---|---|---|---|---|---|---|---|
| 17 | H | CH₃ | 4-CH₃ | H | 2-Cl, 6-CH₃-pyrimidin-4-yl | O | $n_D^{25.0}$ 1.6087 |
| 18 | CH₃ | CH₃ | 2-Cl | H | 2-Cl, 6-CH₃-pyrimidin-4-yl | S | mp 100.0° C. |
| 19 | CH₃ | CH₃ | 2-OCH₃ | H | 2-Cl, 6-CH₃-pyrimidin-4-yl | S | mp 114.5° C. |
| 20 | CH₃ | CH₃ | H | 2-CH₃ | 2-Cl, 6-CH₃-pyrimidin-4-yl | S | mp 91.1° C. |
| 21 | CH₃ | CH₃ | 2-CH₃ | 4-CH₃ | 2-Cl, 6-CH₃-pyrimidin-4-yl | S | mp 215.8° C. |
| 22 | CH₃ | CH₃ | 2-CH₃ | 6-CH₃ | 2-Cl, 6-CH₃-pyrimidin-4-yl | S | mp 147.9° C. |
| 23 | CH₃ | CH₃ | 2-Cl | 6-Cl | 2-Cl, 6-CH₃-pyrimidin-4-yl | S | mp 151.1° C. |
| 24 | CH₃ | CH₃ | 2-Cl | 5-Cl | 2-Cl, 6-CH₃-pyrimidin-4-yl | S | mp 124.8° C. |
| 25 | CH₃ | CH₃ | 2-Cl | H | 6-CH₃-pyrimidin-4-yl | S | $n_D^{22}$ 1.5850 |

TABLE 2-continued

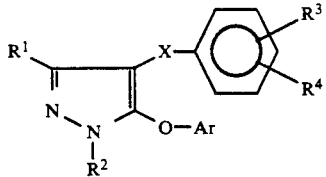

| Comp. No. | $R^1$ | $R^2$ | $R^3$ | $R^4$ | Ar | X | Property |
|---|---|---|---|---|---|---|---|
| 26 | $CH_3$ | $CH_3$ | 2-Cl | H | 2-Cl-pyridin-5-yl | $CH_2$ | mp 57° C. |
| 27 | $CH_3$ | $CH_3$ | H | 4-Cl | 2-Cl-pyridin-5-yl | $CH_2$ | mp 82° C. |
| 28 | $CH_3$ | $CH_3$ | 2-Cl | 4-Cl | 2-Cl-pyridin-5-yl | $CH_2$ | $n_D^{23}$ 1.5990 |
| 29 | $C_2H_5$ | $CH_3$ | 2-Cl | H | 2-Cl-pyridin-5-yl | S | $n_D^{21}$ 1.5980 |
| 30 | $CH_3$ | $C_2H_5$ | 2-Cl | H | 2-Cl-pyridin-5-yl | S | $n_D^{22}$ 1.5950 |
| 31 | $CH_3$ | $C_3H_7(i)$ | 2-Cl | H | 2-Cl-pyridin-5-yl | S | mp 108° C. |
| 32 | $CH_3$ | $CH_3$ | H | 4-$CF_3$ | 2-Cl-pyridin-5-yl | S | mp 110° C. |
| 33 | $CH_3$ | $CH_3$ | 2-Cl | H | 5-$CH_3$-pyrimidin-2-yl | S | mp 102° C. |
| 34 | $CH_3$ | $CH_3$ | 2-Cl | H | 2-$OCH_3$-pyridin-5-yl | S | mp 64° C. |

TABLE 2-continued

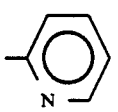

| Comp. No. | $R^1$ | $R^2$ | $R^3$ | $R^4$ | Ar | X | Property |
|---|---|---|---|---|---|---|---|
| 35 | $CH_3$ | $CH_3$ | 2-Cl | H | 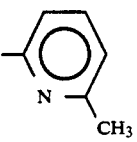 | S | $n_D^{21}$ 1.5700 |
| 36 | $CH_3$ | $CH_3$ | 2-Cl | H | 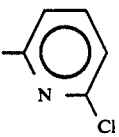 | S | mp 104° C. |
| 37 | $CH_3$ | $CH_3$ | 2-Cl | H | 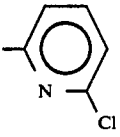 | S | mp 65° C. |
| 38 | $CH_3$ | $C_2H_5$ | 2-Cl | H | 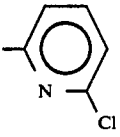 | S | $n_D^{21}$ 1.5799 |
| 39 | $CH_3$ | $CH_3$ | 2-Cl | H | 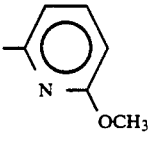 | S | $n_D^{21}$ 1.5665 |
| 40 | $CH_3$ | $CH_3$ | 2-Cl | H | 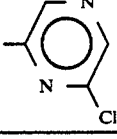 | S | $n_D^{21}$ 1.5830 |

Hereinafter examples of formulation according to the invention are shown. In the following Formulation Examples the term "part(s)" means part(s) by weight.

FORMULATION EXAMPLE 1

Fifty parts of any one of the compounds Nos. 1 to 40, 3 parts of calcium ligninsulfonate, 2 parts of sodium lauryl sulfate and 45 parts of synthetic hydrous silicate were sufficiently pulverized and mixed to obtain a wettable powder.

FORMULATION EXAMPLE 2

Twenty-five parts of any one of the compounds Nos. 1 to 40, 3 parts of polyoxyethylene sorbitan monooleate, 3 parts of CMC and 69 parts of water were mixed. Thus obtained mixture was wetly pulverized until the particle size of the active ingredient became less than 5 microns to obtain a suspension.

FORMULATION EXAMPLE 3

Two parts of any one of the compounds Nos. 1 to 40, 88 parts of kaolin clay and 10 parts of talc were sufficiently pulverized and mixed to obtain a powder formulation.

FORMULATION EXAMPLE 4

Twenty parts of any one of the compounds Nos. 1 to 40, 14 parts of polyoxyethylenestyrylphenyl ether, 6 parts of calcium dodecylbenzenesulfonate and 60 parts of xylene were sufficiently mixed to obtain an emulsion.

FORMULATION EXAMPLE 5

Two parts of any one of the compounds Nos. 1 to 40, 1 part of synthetic hydrous silicate, 2 parts of calcium ligninsulfonate, 30 parts of bentonite and 65 parts of kaolin clay were sufficiently pulverized and mixed. The mixture was kneaded with water, and then granulated and dried to obtain a granule formulation.

Following Test Examples show that the compound of the present invention is useful as an agricultural and/or horticultural fungicide. Also, test compound No. of the present invention corresponds to Compound No. in Table 2, and comparative compound No. corresponds to Compound No. in Table 3.

TABLE 3

| Comp. No. | Chemical structural formula | Note |
|---|---|---|
| A | | Compound described in Japanese Unexamined Patent Publication No. 125379/1989 |
| B | | Compound described in Japanese Unexamined Patent Publication No. 125379/1989 |
| C | | Same as above |
| D | | Same as above |

Control effect of the compounds are illustratively shown in the following Test Examples wherein the states of plant diseases, i.e. mycelial tuft of foliage and stalks and the degree of lesions are observed with the naked eye to rate control effect with an index 5, 4, 3, 2, 1 or 0, in which the numeral "5" indicates no mycelia tuft and no lesion, the numeral "4" indicates approximately 10% mycelia tuft and lesion in comparison with those of untreated plant, the numeral "3" indicates approximately 30% mycelia tuft and lesion in comparison with those of untreated plant, the numeral "2" indicated approximately 50% mycelia tuft and lesion in comparison with those of untreated plant, the numeral "1" indicates approximately 70% mecelia tuft and lesion in comparison with those of untreated plant, and the numeral "0" indicates more than 70% mycelia tuft and lesion and no difference in comparison with untreated plant.

TEST EXAMPLE 1

[Test for controlling sheath blight of rice (preventive effect)]

Plastic pots (volume: 90 ml) were filled with sandy soil and seeds of rice (variety: Kinki No. 33) were sowed therein and grown in a greenhouse for 28 days. A designed amount of a test compound formulated in a wettable powder given according to Formulation Example 1 was obtained by diluting with water. Thus obtained dilution was sprayed over the foliage of a young rice plant to run-off. After spraying, the plant was air-dried and inoculated with pathogenic fungus (Rhizoctonia solani) by spraying mycelia suspension. After the inoculation, the plant was placed at 28° C. under darkness and high humidity for 4 days. As a control the same procedure as the above was carried out except that no test compound was applied to obtain an untreated plant. Then control effect was estimated.

The results are shown in Table 4.

TABLE 4

| Compound No. | Concentration of used compound (ppm) | Control effect |
| --- | --- | --- |
| 1 | 400 | 5 |
| 2 | 400 | 5 |
| 3 | 400 | 5 |
| 4 | 400 | 5 |
| 6 | 400 | 5 |
| 7 | 400 | 5 |
| 9 | 400 | 5 |
| 10 | 400 | 5 |
| 11 | 400 | 5 |
| 12 | 400 | 5 |
| 13 | 400 | 5 |
| 14 | 400 | 5 |
| 15 | 400 | 5 |
| 16 | 400 | 5 |
| 17 | 400 | 5 |
| 18 | 400 | 5 |
| 19 | 400 | 5 |
| 20 | 400 | 5 |
| 22 | 400 | 5 |
| 25 | 400 | 5 |
| 26 | 400 | 5 |
| 27 | 400 | 5 |
| 28 | 400 | 5 |
| 29 | 400 | 5 |
| 30 | 400 | 5 |
| 31 | 400 | 5 |
| 33 | 400 | 5 |
| 34 | 400 | 5 |
| 35 | 400 | 5 |
| 36 | 400 | 5 |
| 37 | 400 | 5 |
| 39 | 400 | 5 |
| 40 | 400 | 5 |

TEST EXAMPLE 2

[Test for controlling apple scab (preventive effect)]

Plastic pots (volume: 90 ml) were filled with sandy soil and seeds of apple were sowed therein and grown in a greenhouse for 20 days. A designed amount of a test compound formulated in a suspension given according to Formulation Example 2 was obtained by diluting with water. Thus obtained dilution was sprayed over the foliage of a young apple plant to run-off. After air-drying, the plant was inoculated with pathogenic fungus (*Venturia inaequalis*) by spraying spore suspension. After the inoculation, the plant was placed at 15° C. under high humidity for 4 days. Further the plant was grown under lighting for 15 days. As a control the same procedure as the above was carried out except that no test compound was applied to obtain an untreated plant. The control effect was estimated.

The results are shown in Table 5.

TABLE 5

| Compound No. | Concentration of used compound (ppm) | Control effect |
| --- | --- | --- |
| 2 | 400 | 5 |
| 5 | 400 | 5 |
| 8 | 400 | 5 |
| 15 | 400 | 5 |
| 16 | 400 | 5 |
| 18 | 400 | 5 |
| 20 | 400 | 5 |
| 23 | 400 | 5 |
| 25 | 400 | 5 |
| 29 | 400 | 5 |

TABLE 5-continued

| Compound No. | Concentration of used compound (ppm) | Control effect |
| --- | --- | --- |
| 30 | 400 | 5 |

TEST EXAMPLE 3

[Test for controlling gray mold of cucumber (preventive effect)]

Plastic pots (volume: 90 ml) were filled with sandy soil and seeds of cucumber (*Sagami hanjiro*) were sowed therein and grown in a greenhouse for 14 days. A designed amount of a test compound formulated in a wettable powder given according to Formulation Example 1 was obtained by diluting with water. Thus obtained dilution was sprayed over the foliage of a young cucumber plant to run-off. After spraying, the plant was air-dried and inoculated with mycelia of pathogenic fungus (*Botrytis cinerea*) resistant to MBC (carbendazim). After the inoculation the plant was placed at 15° C. under darkness and high humidity for 3 days. As a control the same procedure as the above was carried out except that no test compound was applied to obtain an untreated plant. Then control effect was estimated.

The results are shown in Table 6.

TABLE 6

| Compound No. | Concentration of used compound (ppm) | Control effect |
| --- | --- | --- |
| 1 | 200 | 5 |
| 10 | 200 | 5 |
| 18 | 200 | 5 |
| " | 50 | 5 |
| 20 | 200 | 5 |
| 21 | 200 | 5 |
| 24 | 200 | 5 |
| 25 | 200 | 5 |
| 26 | 200 | 5 |
| 28 | 200 | 5 |
| 29 | 200 | 5 |
| 30 | 200 | 5 |
| " | 50 | 5 |
| 32 | 200 | 5 |
| 37 | 200 | 5 |
| 38 | 200 | 5 |
| 40 | 200 | 5 |
| A | 200 | 2 |
| B | 200 | 2 |
| C | 200 | 2 |
| D | 200 | 2 |

What we claim is:

1. A compound having the formula I:

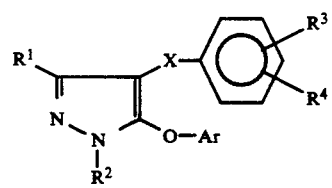

wherein $R^1$ is a lower alkyl group, $R^2$ is a lower alkyl group, $R^3$ and $R^4$ are the same or different and each is a hydrogen atom, a halogen atom, a lower alkyl group, a lower haloalkyl group or a lower alkoxy group, X is an oxygen atom, a sulfur atom or a methylene group, and Ar is a pyrimidine-4-yl group which may be substituted by one or two substituents selected from the group consisting of a halogen atom, a lower alkyl group and a lower alkoxy group.

2. The compound according to claim 1, wherein Ar is a 2-halogenopyrimidine-4-yl group.

3. The compound according to claim 1, wherein X is a sulfur atom.

4. The compound according to claim 2, wherein X is a sulfur atom.

5. The compound according to claim 1, wherein $R^1$ a methyl group and $R^2$ is a methyl group or an ethyl group.

6. The compound according to claim 2, wherein $R^1$ a methyl group and $R^2$ is a methyl group or an ethyl group.

7. The compound according to claim 3, wherein $R^1$ a methyl group and $R^2$ is a methyl group or an ethyl group.

8. The compound according to claim 7, wherein $R^3$ is a 2-halogen atom and $R^4$ is a hydrogen atom.

9. A compound having the formula:

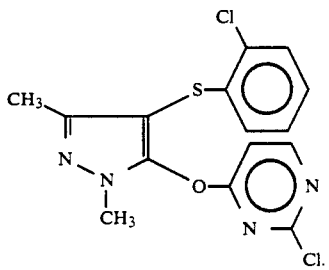

10. A compound having the formula:

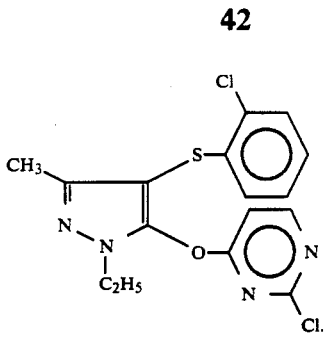

11. An agricultural and/or horticultural fungicidal composition which comprises as an active ingredient a fungicidally effective amount of a compound having the formula I:

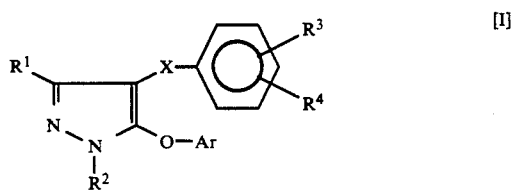

wherein $R^1$ is a hydrogen atom or a lower alkyl group, $R^2$ is a lower alkyl group, $R^3$ and $R^4$ are the same or different each other and each is a hydrogen atom, a halogen atom, a lower alkyl group, a lower haloalkyl group or a lower alkoxy group, X is an oxygen atom, a sulfur atom or a methylene group, and Ar is a pyrimidine-4-yl group which may be substituted by one or two substituents selected from the group consisting of a halogen atom, a lower alkyl group, a lower alkoxy group and a nitro group, and an agriculturally and/or horticulturally acceptable carrier or diluent.

12. A method for preventing plant diseases which comprises applying a fungicidally effective amount of the compound according to claim 1 to plants.

* * * * *